US010370331B2

(12) United States Patent
Masere et al.

(10) Patent No.: US 10,370,331 B2
(45) Date of Patent: Aug. 6, 2019

(54) POLYMERIZATION INHIBITOR COMPOSITIONS

(71) Applicant: Ecolab USA Inc., St. Paul, MN (US)

(72) Inventors: Jonathan Masere, Richmond, TX (US); Javier Florencio, Reus (ES); Ramon Colorado, Jr., Houston, TX (US); Andrew R. Neilson, Richmond, TX (US); David Youdong Tong, Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/915,201

(22) Filed: Mar. 8, 2018

(65) Prior Publication Data
US 2018/0258014 A1 Sep. 13, 2018

Related U.S. Application Data

(60) Provisional application No. 62/469,227, filed on Mar. 9, 2017.

(51) Int. Cl.
| | | |
|---|---|---|
| *C07C 7/20* | (2006.01) | |
| *C07D 211/94* | (2006.01) | |
| *C07C 231/22* | (2006.01) | |
| *C07C 67/62* | (2006.01) | |
| *C07C 51/50* | (2006.01) | |
| *C08F 2/40* | (2006.01) | |

(52) U.S. Cl.
CPC .............. *C07D 211/94* (2013.01); *C07C 7/20* (2013.01); *C07C 51/50* (2013.01); *C07C 67/62* (2013.01); *C07C 231/22* (2013.01); *C08F 2/40* (2013.01)

(58) Field of Classification Search
CPC ........... C07C 7/20; C07C 51/50; C07C 67/62; C07D 211/94; C08F 2/38; C08F 2/40
See application file for complete search history.

(56) References Cited

U.S. PATENT DOCUMENTS

2010/0168434 A1* 7/2010 Loyns ....................... C07C 7/20
  546/242
2015/0337056 A1 11/2015 Koch et al.

FOREIGN PATENT DOCUMENTS

| CN | 104039835 A * | 9/2014 | ........... C07D 211/94 |
| JP | 3207144 B2 | 9/2001 | |
| WO | 99/21893 A2 | 5/1999 | |
| WO | 2013/084443 A1 | 6/2013 | |

OTHER PUBLICATIONS

International Search Report for International Application No. PCT/US2018/021478, dated Jun. 5, 2018, 5 pages.
Written Opinion for International Application No. PCT/US2018/021478, dated Jun. 5, 2018, 8 pages.

* cited by examiner

*Primary Examiner* — Yate' K Cutliff
(74) *Attorney, Agent, or Firm* — Kagan Binder, PLLC

(57) ABSTRACT

Disclosed herein are compositions including between 20 wt % and 50 wt % of a nitroxyl compound such as 2,2,6,6-tetramethylpiperidinyl-1-oxyl. The compositions are stable under field conditions of transportation and storage. The compositions remain homogeneous and pumpable or pourable at temperatures between −20° C. and 60° C., even when temperatures fluctuate in this range over a period of 10 days to 5 years, and even where the container used to transport and store the composition is made from metal or includes a metal surface contacting the composition.

16 Claims, No Drawings

POLYMERIZATION INHIBITOR COMPOSITIONS

TECHNICAL FIELD

The invention is directed to concentrated solutions of polymerization inhibitors that are stable when stored at temperatures varying between −20° C. to 60° C.

BACKGROUND

During production and processing of some chemicals, water is used to control various chemical reactions, for example by transferring heat to quench a reaction. When such water is subjected to direct contact with the reactive, reacting, or reacted chemicals, it is commonly referred to as process water. Process water contacted with petrochemicals often include a variety of polymerizable unsaturated compounds such as styrenes, indene, and isoprene. Polymerization of these species dispersed in the process water leads to eventual deposition of oligomers and polymers on contacted equipment surfaces, referred to as fouling. Fouling reduces energy efficiency of processing systems, reduces processing plant throughput, and gives rise to product quality issues in the process system.

The production and processing of polymerizable unsaturated compounds such as styrenes, isoprenes, acrylates, acrylamides, such as formation, separation or purification e.g. by distillation, and the like also lead to undesirable polymerization in the product stream. Even minor amounts of reaction in such process streams lead to fouling of equipment surfaces, as well as loss of yield of the desired species.

Various approaches are used in the chemical industry to address undesirable or untimely polymerization of unsaturated species in chemical processing streams. In one conventional approach, dispersants (e.g. surfactants or hydrotropes) are employed to keep potential foulants dispersed in a water phase. Another conventional approach is to use a polymerization inhibitor to quench polymerization reactions in situ. One effective polymerization inhibitor is (2,2,6,6-tetramethylpiperidin-1-yl)oxyl, represented by formula I:

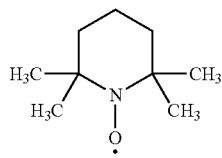

(2,2,6,6-Tetramethylpiperidin-1-yl)oxyl and related structures (collectively, "nitroxyl compounds") are effective for quenching polymerization reactions in aqueous and non-aqueous reactive chemical systems. A standard "dose" for effective inhibition of polymerization in a processing stream might be, for example, 1 ppm to 500 ppm of one or more nitroxyl compounds based on the weight of the processing stream.

Nitroxyl compounds are solids under normal operating laboratory conditions. Operators of chemical processing plants advantageously add such solid chemicals to process streams by applying concentrated solutions or dispersions thereof by applying the process stream to yield the targeted dose of chemical. A suitable concentrate for this purpose provides both ease of end use and efficient transportation and storage of a minimum volume of material. However, ambient outdoor weather conditions present special challenges to those formulating concentrates for application to process streams associated with industrial plants such as petrochemical processing plants. Such concentrates must remain pourable or pumpable and also substantially homogeneous when subjected to temperatures as low as −10° C. or even −20° C. The concentrate must be pourable or pumpable to enable the operator to easily apply the concentrate directly to a process stream using a metering method such as a pump. The concentrate must further deliver a substantially consistent composition to the process stream without any special steps. Therefore inhomogeneity caused by phase separation such as precipitation either renders the concentrate useless or causes the need to use additional steps to reestablish homogeneity, such as mixing or warming or both.

Making a concentrated solution or dispersion of a nitroxyl compound that meets the requirements of such field use is challenging. For example, a solution including 30 wt % or more, for example up to 40 wt %, of 4-hydroxy-(2,2,6,6-tetramethylpiperidin-1-yl)oxyl ("HTMPO") is easily formed under standard laboratory conditions of 1 atmosphere and 25° C. by simple addition to water or water blended with a water miscible solvent. However, these mixtures tend to precipitate and/or gel over time, even at 25° C. Many such compositions also freeze when transported and/or stored at temperatures below 0° C. More dilute solutions or dispersions nitroxyl compounds, such as 5 wt % to 15 wt %, suffer less from precipitation or gelling but still suffer from freezing at temperatures below 0° C.

There remains a need in the industry to provide concentrated solutions or dispersions of nitroxyl compounds having at least 20 wt % solids that are pourable or pumpable and substantially homogeneous under a range of conditions that may be present during actual transportation, storage, and application to process streams in the field.

SUMMARY

Disclosed herein is a composition including a nitroxyl compound, and a method of using the composition. The composition includes about 20 wt % to 50 wt % of the nitroxyl compound and is pourable or pumpable and substantially homogeneous at temperatures between about −20° C. and 60° C. for at least 10 days and up to about five years. The composition is applied by an operator to an industrial process stream using conventional equipment and without any special mixing or blending steps to provide the selected dose. The composition is compatible with industrial process streams and thus dissolves or distributes in homogeneous fashion without taking any action aside from adding the concentrate to a process stream.

The composition comprises, consists essentially of, or consists of about 20 wt % to 50 wt % of a nitroxyl compound or a blend of two or more nitroxyl compounds, about 20 wt % to 30 wt % water, about 25 wt % to 35 wt % diethylene glycol monobutyl ether (2-(2-butoxyethoxy)ethanol; chemical formula: $C_4H_9(OCH_2CH_2)_2OH$), and about 1 wt % to 10 wt % of a hydrocarbon solvent. The hydrocarbon solvent comprises, consists essentially of, or consists of one or more of the following: bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methyl-ethoxy)-propan-1-ol, 2-ethylhexan-1-ol, propane-1,2-diol, and 1-acetoxy-2-butoxyethane. In some embodiments, the nitroxyl compound is 4-hydroxy-2, 2,6,6-tetramethylpiperidin-1-oxyl ("HTMPO"). The composition is substantially homogeneous at temperatures of about −20° C. to 60° C. and over a period of at least about 10 days to 5 years. The composition is pourable, pumpable, or both at temperatures of about −20° C. to 60° C. and over a period of at least about 10 days to 5 years.

Also disclosed herein is a method of using a composition, the method comprising or consisting essentially of a) forming a composition comprising, consisting essentially of, or consisting of about 20 wt % to 50 wt % of a nitroxyl compound or a blend of two or more thereof, about 20 wt % to 30 wt % water, about 25 wt % to 35 wt % diethylene glycol monobutyl ether, and about 1 wt % to 10 wt % of a hydrocarbon solvent comprising, consisting essentially of, or consisting of one or more of the following: bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methylethoxy)-propan-1-ol, 2-ethylhexan-1-ol, propane-1,2-diol, and 1-acetoxy-2-butoxyethane; b) storing the composition in an enclosed container for a period of about 10 days to 5 years under conditions wherein the composition reaches a temperature between 0° C. and −20° C. at least once during the storage period; c) removing the composition from the container by pumping or pouring; and d) applying the composition to an industrial process stream.

In some embodiments the removing, the applying, or both are carried out at a temperature between 0° C. and −20° C. In some embodiments, the method further includes transporting the composition; in some such embodiments the transporting includes transporting at a temperature between 0° C. and −20° C. In some embodiments the container used for storing comprises, consists essentially of, or consists of metal, further wherein at least a portion of a surface contacting the composition includes the metal. In some such embodiments, the metal comprises one or more of aluminum, iron, or chromium; in some such embodiments the metal comprises, consists essentially of, or consists of an alloy having greater than 10.5 wt % chromium.

Additional advantages and novel features of the invention will be set forth in part in the description that follows, and in part will become apparent to those skilled in the art upon examination of the following, or may be learned through routine experimentation upon practice of the invention.

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Definitions

As used herein, the term "process stream" means a chemical processing stream (e.g. chemicals disposed within or otherwise in contact with a reactor, addition port, condenser, heated unit, mixing unit, or other unit or associated piping and other conduits intended for chemical synthesis, purification, separation, mixing, addition, and the like) that includes one or more unsaturated polymerizable compounds. Unsaturated polymerizable compounds include α,β-unsaturated radically polymerizable compounds and mixtures thereof. Commonly employed but nonlimiting examples of unsaturated polymerizable compounds include acrylic acid, acrylate esters, acrylamide, styrene, and isoprene. The process stream may consist of, or consist essentially of one or more unsaturated polymerizable compounds, or may include as little as 1 ppm of one or more unsaturated polymerizable compounds. The process stream is aqueous or substantially non-aqueous, and is present within a continuous, semi-continuous, or batch type processing stream.

As used herein, the terms "pumpable", "pourable", "flow" or like terms referring to a composition of the invention means that 10 mL of the composition vertically at rest on a substantially horizontal surface in a cylindrical container having dimensions of radius 1 inch and height 2 inches flows observably within about 10 seconds when tipped to a substantially horizontal position. In some embodiments, "pumpable", "pourable", "flow", or like terms referring to a composition of the invention means a composition having a Brookfield viscosity at 10 $s^{-1}$ of about 5 cP to 1000 cP.

As used herein, the term "concentrate" means a combination including at least a nitroxyl compound and a liquid, wherein the nitroxyl compound is present at 15 wt % or greater and the combination is a solution or dispersion of the nitroxyl compound.

As used herein, the term "container" or similar terms means a vessel that holds or contains a composition, wherein the vessel is substantially enclosed. In embodiments the container is a bottle, can, jar, drum, carboy, or the like; or it is a shipping container, truck bed, or the like. The composition is placed in the container for purposes of transportation, storage, or both. Storage in a container further contemplates the use of the container to deliver a portion of the composition therein to a process water.

As used herein, the term "stable" or "homogeneous" referring to a composition of the invention means that the composition is substantially free of visual evidence of gel formation or phase separation.

"Conditions of transportation and/or storage in the field", "ambient weather conditions" and similar phrases indicating field transportation, storage, or use of a composition of the invention means a) a temperature range of −20° C. to 60° C.; b) a temporal range of about 10 days to 5 years; or c) a temperature range of −20° C. to 60° C. over a temporal range of about 10 days to 5 years, further wherein temperature is variable within the range over the period.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

As used herein, the term "substantially" means "consisting essentially of", as that term is construed in U.S. patent law, and includes "consisting of" as that term is construed in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Compositions

Disclosed herein is a composition comprising, consisting essentially of, or consisting of one or more nitroxyl compounds, water, diethylene glycol monobutyl ether, and one or more hydrocarbon solvents. In embodiments, the composition includes about 20 wt % to 50 wt % of a nitroxyl compound or blend thereof, for example about 25 wt % to 50 wt %, or about 30 wt % to 50 wt %, or about 35 wt % to 50 wt %, or about 40 wt % to 50 wt %, or about 20 wt % to 45 wt %, or about 20 wt % to 40 wt %, or about 20 wt % to 35 wt %, or about 20 wt % to 30 wt %, or about 25 wt % to 45 wt %, or about 25 wt % to 40 wt %, or about 30 wt % to 45 wt %, or about 30 wt % to 40 wt %, or about 35 wt % to 45 wt %, of a nitroxyl compound or a blend of two or more thereof.

In embodiments, the nitroxyl compound is water soluble or water dispersible and includes an N—O. or N—OH moiety. Exemplary but non-limiting examples of nitroxyl compounds include 2,2,6,6-tetramethylpiperidinyl-1-oxyl (TEMPO), 1-hydroxy-2,2,6,6-tetramethylpiperidine (TEMPOH), 4-hydroxy-2,2,6,6-tetramethylpiperidinyl-1-oxyl (HTMPO), 4-oxo-2,2,6,6-tetramethylpiperidinyl-1-oxyl (OTEMPO), 1,4-dihydroxy-2,2,6,6-tetramethylpiperidine (HTMPOH), and 1-hydroxy-4-oxo-2,2,6,6-tetramethylpiperidine (OTEMPOH). Blends of two or more nitroxyl compounds are similarly useful and the relative proportion thereof in the composition is not particularly limited.

In embodiments, the composition includes about 20 wt % to 30 wt % water, for example about 22 wt % to 30 wt %, or about 24 wt % to 30 wt %, or about 26 wt % to 30 wt %, or about 20 wt % to 28 wt %, or about 20 wt % to 26 wt %, or about 22 wt % to 28 wt %, or about 24 wt % to 26 wt % water. In embodiments, the composition includes about 25 wt % to 35 wt % diethylene glycol monobutyl ether, or $C_4H_9(OCH_2CH_2)_2OH$, for example about 26 wt % to 35 wt %, or about 27 wt % to 35 wt %, or about 28 wt % to 35 wt %, or about 29 wt % to 35 wt %, or about 30 wt % to 35 wt %, or about 31 wt % to 35 wt %, or about 32 wt % to 35 wt %, or about 33 wt % to 35 wt %, or about 34 wt % to 35 wt %, or about 25 wt % to 34 wt %, or about 25 wt % to 33 wt %, or about 25 wt % to 32 wt %, or about 25 wt % to 31 wt %, or about 25 wt % to 30 wt %, or about 25 wt % to 29 wt %, or about 25 wt % to 28 wt %, or about 25 wt % to 27 wt %, or about 25 wt % to 26 wt % diethylene glycol monobutyl ether.

The composition includes about 1 wt % to 10 wt % of a hydrocarbon solvent, for example about 2 wt % to 10 wt %, or about 3 wt % to 10 wt %, or about 4 wt % to 10 wt %, or about 5 wt % to 10 wt %, or about 6 wt % to 10 wt %, or about 7 wt % to 10 wt %, or about 8 wt % to 10 wt %, or about 9 wt % to 10 wt %, or about 1 wt % to 9 wt %, or about 1 wt % to 8 wt %, or about 1 wt % to 7 wt %, or about 1 wt % to 6 wt %, or about 1 wt % to 5 wt %, or about 1 wt % to 4 wt %, or about 1 wt % to 3 wt %, or about 1 wt % to 2 wt % of a hydrocarbon solvent. The hydrocarbon solvent comprises, consists essentially of, or consists of one or more of the following: bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methyl-ethoxy)-propan-1-ol, 2-ethylhexan-1-ol, propane-1,2-diol, 1-acetoxy-2-butoxy-ethane, or two or more thereof in any proportion.

The composition is pourable or pumpable and substantially homogeneous when formed by simple admixing. In embodiments, the composition is stored in a container between forming and applying the composition to a process stream. In some embodiments, the container includes a metal surface contacting the composition. The composition is advantageously stored in the container for at least 10 (ten) days and up to 5 (five) years in ambient weather conditions, where "ambient weather conditions" indicates that the storage is conducted without any effort to regulate temperature of the composition, such as by heating or cooling a container holding the composition, or by heating or cooling a storage facility housing the container. In embodiments, ambient weather conditions can lead to a composition temperature of about 0° C. to −20° C., or about 0° C. to −10° C. for at least some portion of the storage period, up to and including the entirety of the storage period. During the storage period in ambient weather conditions, and at the end of the storage period, the composition is pourable or pumpable and is also substantially homogeneous.

The composition remains pumpable or pourable and is stable at temperatures between about −20° C. and 60° C., for example about −19° C. to 60° C., or about −18° C. to 60° C., or about −17° C. to 60° C., or about −16° C. to 60° C., or about −15° C. to 60° C., or about −14° C. to 60° C. or about −13° C. to 60° C. or about −12° C. to 60° C. or about −11° C. to 60° C. or about −10° C. to 60° C., or about −9° C. to 60° C. or about −8° C. to 60° C. or about −7° C. to 60° C. or about −6° C. to 60° C. or about −5° C. to 60° C. for at least 10 days and up to about 5 years, for example about 30 days to 5 years, or about 180 days to 5 years, or about 1 year to 5 years, or about 2 years to 5 years, or about 10 days to 4 years, or about 10 days to 3 years, or about 10 days to 2 years, or about 10 days to 1 year, or about 10 days to 180 days. The compositions are stable over this time period, wherein the temperature varies within a range stated above over this period.

The container enclosing the composition may be placed onsite in the field, in a designated indoor or outdoor storage area, or another convenient arrangement. In some embodiments, the container used to contain the composition is also used for transportation; in such embodiments the period of storage includes the period of transportation. In some embodiments, during the storage period the container is opened and an aliquot of the concentrate removed, then the container is reclosed and stored for an additional length of time. In other embodiments, during the storage period the container is opened and some or substantially all of the concentrate is removed and placed in a different container—for example, where a first container is used to transport the composition and a second container is used to store the composition in the field. The term "storage period" generally refers to the entirety of the time at least some portion of the composition remains in a container. Stated differently, the "storage period" lasts from the time the composition is formed until the time it is applied to a process stream.

The materials employed in the container are not particularly limited. In some embodiments the container comprises, consists essentially of, or consists of a synthetic polymer material such as a polyolefin, polyurethane, polyamide, or polyester. In some embodiments the container comprises, consists essentially of, or consists of glass (such as borosilicate glass). In some embodiments the container comprises, consists essentially of, or consists of a metal. In some embodiments at least a portion of a container surface contacting the composition comprises, consists essentially of, or consists of metal. In some embodiments, the metal comprises one or more of aluminum, iron, or chromium; in some such embodiments the metal comprises, consists essentially of, or consists of an alloy having greater than 10.5 wt % chromium. In some embodiments, the container comprises, consists essentially of, or consists of a stainless steel.

The compositions are also stable up to about 60° C. and do not build up substantial pressure at when stored in an enclosed container at this temperature. The solvent system employed in the compositions has a sufficiently low overall vapor pressure to avoid pressure buildup in ambient weather conditions in the field. Further, the compositions remain pumpable, pourable, and stable/homogeneous at temperatures up to at least 60° C.

Methods

Also disclosed herein are methods of using a composition. In embodiments, the method comprises or consists essentially of a) forming a composition comprising, consisting essentially of, or consisting of about 20 wt % to 50 wt % of a nitroxyl compound or a blend of two or more thereof, about 20 wt % to 30 wt % water, about 25 wt % to 35 wt % diethylene glycol monobutyl ether, and about 1 wt % to 10 wt % of a hydrocarbon solvent comprising, consisting essentially of, or consisting of one or more of the following: bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methyl-ethoxy)-propan-1-ol, 2-ethylhexan-1-ol, propane-1,2-diol, and 1-acetoxy-2-butoxy ethane; b) storing the composition in an enclosed container for a period of about 10 days to 5 years under conditions wherein the composition reaches a temperature between 0° C. and −20° C. at least once during the storage period; c) removing the composition from the container by pumping or pouring; and d) applying the composition to an industrial process stream to form a treated process stream.

In embodiments, the container includes a metal surface contacting the composition; in some such embodiments the metal surface comprises, consists essentially of, or consists of stainless steel. In embodiments, the conditions wherein the composition reaches a temperature between 0° C. and −20° C. at least once during the storage period includes ambient weather conditions. In embodiments, the conditions wherein the composition reaches a temperature between 0° C. and −20° C. at least once during the storage period include conditions wherein the temperature varies between about −20° C. and 60° C., or between about −10° C. and 60° C. over the storage period of about 10 days to 5 years.

The composition is removed from the container and applied to an industrial process stream by an operator using conventional equipment and without any special mixing or blending steps to provide the selected dose to the process stream. The selected dose provides a conventional dose of the nitroxyl compound to the process stream to form a treated process stream. In embodiments the dose is selected to provide a treated process stream including about 1 ppm to 1000 ppm by weight of the nitroxyl compound, for example about 10 ppm to 1000 ppm, or about 100 ppm to 1000 ppm, or about 200 ppm to 1000 ppm, or about 300 ppm to 1000 ppm, or about 400 ppm to 1000 ppm, or about 500 ppm to 1000 ppm, or about 1 ppm to 900 ppm, or about 1 ppm to 800 ppm, or about 1 ppm to 700 ppm, or about 1 ppm to 600 ppm, or about 1 ppm to 500 ppm, or about 1 ppm to 400 ppm, or about 1 ppm to 300 ppm, or about 1 ppm to 200 ppm, or about 1 ppm to 100 ppm, or about 10 ppm to 500 ppm, or about 10 ppm to 400 ppm, or about 10 ppm to 300 ppm, or about 10 ppm to 200 ppm, or about 10 ppm to 100 ppm, or about 50 ppm to 500 ppm, or about 50 ppm to 400 ppm, or about 50 ppm to 300 ppm, or about 50 ppm to 200 ppm, or about 50 ppm to 100 ppm by weight of the nitroxyl compound.

The composition is applied to a process stream employing conventional techniques and equipment well known to the skilled artisan. Thus the composition is easily used to form a treated process stream. In some embodiments, the composition is pumped, for example using a metering pump or the like. In other embodiments, the composition is poured, for example into a feeder that meters the composition into a process stream using gravity. In some embodiments, the process stream is part of a dynamic system and the applying of the composition to the process stream is continuous. In other embodiments, the applying of the composition to the process stream is batchwise.

The process stream includes, in any one or more embodiments, between about 1 ppm and 1,000,000 ppm of one or more unsaturated polymerizable species. The process stream is any industrial process stream including one or more polymerizable unsaturated compounds. In some embodiments, the process stream is a process water that includes one or more polymerizable unsaturated compounds. In petrochemical process waters, for example, one or more polymerizable unsaturated compounds are often present and dispersed therein; species commonly found in such process waters include styrene, indene, and isoprene. In some embodiments a process water further includes one or more industrial waste products and/or additional treatment chemicals. Additional treatment chemicals include but are not limited to conventional chemicals added to industrial process waters to prevent or retard corrosion, provide biocidal activity, maintain the dispersed state of otherwise insoluble materials, or sequester another material from the water phase. In some other embodiments, the process stream is a production or processing stream of one or more polymerizable unsaturated compounds such as styrene, acrylic acid, an acrylate ester, acrylamide, isoprene, an α-olefin, and the like and is directed to the processing thereof, such as synthesis, separation, or purification thereof.

The composition is compatible with one or more process streams and thus dissolves or distributes in homogeneous fashion when applied thereto. In embodiments an operator does not need to take any special steps, and the composition may simply be applied to the concentrate to a process stream. In embodiments, a process stream is present at a temperature between 0° C. and 100° C., wherein the composition is applied thereto at any temperature over this range.

The presently disclosed methodology was developed in response to the observed failure of conventional nitroxyl compound concentrates to remain stable during transportation and/or storage in the field. Conventional concentrates of nitroxyl compounds, including water or various ratios of water and water miscible solvents, suffer from instabilities observed over time and/or with variation in temperature during transportation and storage in the field. We have observed that during transportation and storage in the field, these concentrates may form gels that cannot be pumped or poured; or the nitroxyl compound may precipitate from the concentrate; or both. Unexpectedly, the present compositions solve the foregoing problems, thereby enabling transportation and storage in the field of a stable composition containing up to 50 wt % nitroxyl compound. The compositions remain stable during transportation and storage in the field.

Additionally, we have observed that the instability of conventional nitroxyl compound concentrates are exacerbated in some cases by storage in containers wherein the concentrate contacts a metal surface, for example a stainless steel surface. This previously unarticulated problem is solved by the present compositions and methods.

Additionally, without being limited by theory, it is contemplated that seed crystals present or formed in a nitroxyl compound concentrate, in any type of container, may further act to nucleate observable precipitate. Unlike conventional nitroxyl compound concentrates, the present compositions are stable in the presence of seed crystals of nitroxyl compound. Even further, we have found that the concentrates comprising seed crystals are stable when stored in contact with a metal surface, and do not form any additional observable precipitate under such conditions.

The following examples are intended to show experimental embodiments of the invention. The embodiments are not limiting to the scope of the claims appended hereto. It will be recognized that various modifications and changes may be made without following the experimental embodiments described herein, further without departing from the scope of the claims.

Experimental

Cold Test Procedure

A 30 mL test tube was charged with 0.5 g of HTEMPO crystals and about 1 g of a steel mesh. Then 10 mL of a formulation to be tested was added to the test tube. The tube was capped and placed in a chilled bath, wherein the samples were cooled to about −10° C. and maintained at this temperature for a period of about 16 hours. At the end of the 16 hour period and while the sample remained at −10° C., it was observed and assessed for evidence of freezing, gelation, and precipitation and rated according to the following rating scale: 0=completely gelled or frozen; 1=significant gelation or precipitation; 2=moderate gelation or precipitation; 3=minor amounts of gelation or precipitation; 4=no observable gelation or precipitation. A test rating of 4 indicates "passing".

All amounts recited herein relate to parts by weight or weight percent, unless otherwise specified.

Examples 1-7

An admixture of 40 parts 4-hydroxy-(2,2,6,6-tetramethylpiperidin-1-yl)oxyl (HTMPO), 25 parts water, and 30 parts diethylene glycol monobutyl ether (also known as 2-(2-butoxyethoxy)ethanol) was formed, then divided into seven aliquots. The compounds of Table 1 were added at 5 parts, along with 95 parts of the admixture, to form each of the Examples as shown. These Examples were tested according to the Cold Test Procedure and the results are shown in Table 1.

TABLE 1

Components of Examples 1-7 and results of cold testing.

| Example | Compound added at 5 parts by weight | Cold test rating |
|---|---|---|
| 1 | Bis(2-hydroxyethyl) ether | 3 |
| 2 | Dimethylbenzene-1,2-dicarboxylate | 4 |
| 3 | 4-Methyl-1,3-dioxolan-2-one | 4 |
| 4 | Mixture of 4-oxa-2,6-heptandiol, 2-(2-hydroxy-propoxy)-propan-1-ol, and 2-(2-hydroxy-1-methyl-ethoxy)-propan-1-ol | 4 |
| 5 | 2-Ethyl hexan-1-ol | 4 |
| 6 | Propane-1,2-diol | 4 |
| 7 | 1-Acetoxy-2-butoxyethane | 4 |

Comparative Examples 1-7

The mixtures shown in Table 2 were formed and tested according to the Cold Test Procedure above, and the resulting ratings are also shown in Table 2. The results show that while some ternary solvent combinations pass the cold test at 35 wt % HTMPO, otherwise identical compositions do not pass when the HTMPO concentration is increased to 40 wt %.

TABLE 2

Components of Comparative Examples C1-C7 and results of cold testing. All recited material amounts are in parts by weight.

| Comp. Ex. | HTMPO | Water | Diethylene glycol monobutyl ether | Ethylene glycol | Cold test rating |
|---|---|---|---|---|---|
| 1C | 35 | 21.6 | 21.7 | 21.7 | 3 |
| 2C | 35 | 30 | 30 | 5 | 4 |
| 3C | 35 | 25 | 30 | 10 | 4 |
| 4C | 40 | 25 | 30 | 5 | 2 |
| 5C | 40 | 20 | 30 | 10 | 0 |
| 6C | 40 | 20 | 35 | 5 | 2 |
| 7C | 40 | 20 | 20 | 20 | 0 |

The invention illustratively disclosed herein can be suitably practiced in the absence of any element which is not specifically disclosed herein. Additionally each and every embodiment of the invention, as described herein, is intended to be used either alone or in combination with any other embodiment described herein as well as modifications, equivalents, and alternatives thereof. In various embodiments, the invention suitably comprises, consists essentially of, or consists of the elements described herein and claimed according to the claims. It will be recognized that various modifications and changes may be made without following the example embodiments and applications illustrated and described herein, and without departing from the scope of the claims.

What is claimed is:

1. A composition comprising about 30 wt % to 50 wt % of one or more nitroxyl compounds;
   about 20 wt % to 30 wt % water;
   about 25 wt % to 35 wt % diethylene glycol monobutyl ether; and
   about 1 wt % to 10 wt % of a hydrocarbon solvent, the hydrocarbon solvent comprising one or more of bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methyl-ethoxy)-propan-1-ol, 2-ethylhexan-1-ol, propane-1,2-diol, and 1-acetoxy-2-butoxyethane.

2. The composition of claim 1 wherein the composition comprises about 35 wt % to 50 wt % of the one or more nitroxyl compounds.

3. The composition of claim 1 wherein the composition comprises about 40 wt % to 50 wt % of the one or more nitroxyl compounds.

4. The composition of claim 1 wherein the one or more nitroxyl compounds are selected from 2,2,6,6-tetramethylpiperidinyl-1-oxyl, 1-hydroxy-2,2,6,6-tetramethylpiperidine, 4-hydroxy-2,2,6,6-tetramethylpiperidinyl-1-oxyl, 4-oxo-2,2,6,6-tetramethylpiperidinyl-1-oxyl, 1,4-dihydroxy-2,2,6,6-tetramethylpiperidine, 1-hydroxy-4-oxo-2,2,6,6-tetramethylpiperidine.

5. The composition of claim 1 wherein the one or more nitroxyl compounds consists essentially of 4-hydroxy-2,2,6,6-tetramethylpiperidinyl-1-oxyl.

6. The composition of claim 1 wherein the composition is enclosed in a container.

7. The composition of claim 6 wherein the container comprises a metal surface contacting the composition.

8. The composition of claim 7 wherein the metal is a stainless steel.

9. The composition of claim 1 wherein the composition is stable and is pumpable or pourable between −20° C. and 60° C.

10. The composition of claim 1 wherein the composition is stable and is pumpable or pourable between −10° C. and 60° C.

11. The composition of claim 1 wherein the composition is stable and is pumpable or pourable for a period of about 10 days to 5 years.

12. The composition of claim 1 wherein the composition is stable and is pumpable or pourable over a temperature range of −20° C. to 60° C. and a temporal range of about 10 days to 5 years, further wherein the temperature varies within the temperature range over the temporal range.

13. A method comprising
   a) forming a composition comprising about 20 wt % to 50 wt % of one or more nitroxyl compounds, about 20 wt % to 30 wt % water, about 25 wt % to 35 wt % diethylene glycol monobutyl ether, and about 1 wt % to 10 wt % of a hydrocarbon solvent, the hydrocarbon solvent comprising one or more of bis(2-hydroxyethyl) ether, dimethyl benzene-1,2-dicarboxylate, 4-methyl-1,3-dioxolan-2-one, 4-oxa-2,6-heptandiol, 2-(2-hydroxy-propoxy)-propan-1-ol, 2-(2-hydroxy-1-methyl-ethoxy)-propan-1-ol, 2-ethylhexan-1-ol, propane-1,2-diol, and 1-acetoxy-2-butoxyethane;
   b) storing the composition in an enclosed container for a period of about 10 days to 5 years under conditions wherein the composition reaches a temperature between 0° C. and 20° C. at least once during the storage period;
   c) removing the composition from the container by pumping or pouring; and
   d) applying the composition to an industrial process stream comprising one or more unsaturated polymerizable compounds.

14. The method of claim 13 wherein the removing, the applying, or both are carried out at a temperature between 0° C. and −20° C.

15. The method of claim 13 wherein the method further includes transporting the composition.

16. The method of claim 13 wherein the container comprises a metal surface and storing the composition comprises contacting the composition with the metal surface.

* * * * *

UNITED STATES PATENT AND TRADEMARK OFFICE
CERTIFICATE OF CORRECTION

PATENT NO. : 10,370,331 B2
APPLICATION NO. : 15/915201
DATED : August 6, 2019
INVENTOR(S) : Jonathan Masere et al.

It is certified that error appears in the above-identified patent and that said Letters Patent is hereby corrected as shown below:

In the Claims

Column 12, Claim 13, Line 28, "20° C.", should be -- -20° C. --

Signed and Sealed this
Eighth Day of November, 2022

Katherine Kelly Vidal
*Director of the United States Patent and Trademark Office*